United States Patent
Godau et al.

(10) Patent No.: US 7,835,788 B1
(45) Date of Patent: Nov. 16, 2010

(54) IMPLANTABLE CARDIAC DEVICE PROVIDING INTRINSIC CONDUCTION ENCOURAGEMENT AND METHOD

(75) Inventors: Arndt Godau, Los Angeles, CA (US);
Donald S. Cogan, Saugus, CA (US);
Gene A. Bornzin, Simi Valley, CA (US);
Sharon Standage, Palmdale, CA (US);
Kiersten Hathaway, Panora, IA (US)

(73) Assignee: Pacesetter, Inc., Sylmar, CA (US)

( * ) Notice: Subject to any disclaimer, the term of this patent is extended or adjusted under 35 U.S.C. 154(b) by 788 days.

(21) Appl. No.: 11/316,082

(22) Filed: Dec. 21, 2005

(51) Int. Cl.
*A61N 1/362* (2006.01)
(52) U.S. Cl. .................. 607/9; 607/4; 607/14; 607/17
(58) Field of Classification Search .................. 607/4, 607/5, 9, 14, 17
See application file for complete search history.

(56) References Cited

U.S. PATENT DOCUMENTS

| 5,237,992 | A | * | 8/1993 | Poore | 607/18 |
| 5,282,838 | A | * | 2/1994 | Hauser et al. | 607/9 |
| 5,374,281 | A | * | 12/1994 | Kristall et al. | 607/17 |
| 6,498,950 | B1 | | 12/2002 | Bradley | 607/27 |
| 6,772,005 | B2 | | 8/2004 | Casavant et al. | 607/4 |
| 7,065,406 | B1 | * | 6/2006 | Gustavsson | 607/11 |
| 2002/0082646 | A1 | | 6/2002 | Casavant et al. | 607/9 |
| 2003/0078627 | A1 | | 4/2003 | Casavant et al. | 607/9 |
| 2004/0143299 | A1 | | 7/2004 | Casavant et al. | 607/9 |
| 2004/0147966 | A1 | | 7/2004 | Ding et al. | 607/9 |
| 2004/0215262 | A1 | * | 10/2004 | Ferek-Petric | 607/17 |
| 2005/0010255 | A1 | * | 1/2005 | Oosterhoff et al. | 607/9 |

FOREIGN PATENT DOCUMENTS

| WO | WO 02/051499 A1 | 7/2002 |
| WO | WO 2004/026397 A1 | 4/2004 |
| WO | WO 2004/069333 A2 | 8/2004 |
| WO | WO 2004/069333 A3 | 8/2004 |

* cited by examiner

*Primary Examiner*—Carl H Layno
*Assistant Examiner*—Jennifer Stewart

(57) ABSTRACT

An implantable cardiac stimulation device promotes intrinsic activity of a heart during demand pacing. The device increases the time and probability of an AV delay interval extension. The device may further increase the AV delay interval from a first extended AV delay interval to a longer second extended AV delay interval. The device may further encourage intrinsic AV conduction in patients with intact AV conduction by allowing multiple cycles during a search interval and multiple search times to further encourage intrinsic conduction from the atrium to the ventricle.

12 Claims, 5 Drawing Sheets

IMPLANTABLE CARDIAC DEVICE PROVIDING INTRINSIC CONDUCTION ENCOURAGEMENT AND METHOD

FIELD OF THE INVENTION

The present invention generally relates to an implantable cardiac device. The present invention more particularly relates to an implantable pacemaker which encourages intrinsic conduction of a patient's heart.

BACKGROUND OF THE INVENTION

Implantable cardiac devices are well known in the art. They may take the form of implantable defibrillators or cardioverters which treat accelerated rhythms of the heart such as fibrillation. They may also take the form of implantable pacemakers which maintain the heart rate above a prescribed limit, such as, for example, to treat a bradycardia. Implantable cardiac devices are also known which incorporate both a pacemaker and a defibrillator.

A pacemaker is comprised of two major components. One component is a pulse generator which generates the pacing stimulation pulses and includes the electronic circuitry and the power cell or battery. The other component is the lead, or leads, which electrically couple the pacemaker to the heart.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses the same chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode. Further, pacing systems are known which pace in multiple sites. For example, biventricular pacing paces in both ventricles and biatrial pacing paces in both atria. Hence, it is possible, that a heart may be paced in all four of its chambers.

A popular mode of operation for dual-chamber pacemakers is the DDD mode. Specifically, DDD systems provide atrial pacing during atrial bradycardia, ventricle pacing during ventricular bradycardia, and atrial and ventricular pacing during combined atrial and ventricular bradycardia or heart block also known as AV block. In addition, DDDR systems monitor patient activity levels for controlling pacing rate to more closely approximate the normal response of the heart to exercise, or other physiological activity demanding a faster heart rate.

A recent study has indicated, however, that ventricular pacing in the setting of intact AV nodal conduction has an adverse impact compared to permitting intrinsic ventricular contractions. Hence, pacing therapies have been advanced which encourage intrinsic ventricular activity.

One such system employs an auto intrinsic conduction search (AICS) wherein the pacemaker utilizes two AV intervals. The first interval is a programmable base AV interval to support ventricular demand pacing. It may be, for example, on the order of two hundred (200) milliseconds. The second AV interval is an extended AV interval which may be thought of as comprising the base AV interval with an AV interval extension added to its end. The AV interval extension may be on the order of one hundred (100) milliseconds, for example. Hence, in this example, the extended AV interval would total three hundred (300) milliseconds.

The AICS may be implemented as follows. The device paces in a demand mode with the base AV interval. After a search interval of five minutes, for example, the device extends the AV interval to the extended AV interval for one cycle to encourage intrinsic ventricular activity. The device does not reset to the shorter base AV interval until a ventricular pacing pulse is administered.

Other methods to promote or encourage intrinsic conduction have been advanced. One proposed method is based upon mode switching from a DDD(R) mode to an AAI(R) to more aggressively promote intrinsic conduction. Unfortunately, this concept has disadvantages. Methods which switch to an atrial pacing mode like AAIR can create the loss of one or more ventricular contractions before the mode is switched back to a dual-chamber mode. The loss of the ventricular contraction might create symptoms which patients might find difficult tolerate. Depending on the criteria used to switch back to the dual-chamber mode, a hemodynamically compromising situation (with a too slow intrinsic conduction) can result for a longer period of time in the atrial pacing (AAIR) mode.

Another proposed method is to provide prolonged AV interval. A prolonged AV interval reduces the available programmable values for the Maximum Tracking Rate (MTR), if the post ventricular atrial refractory period (PVARP) is not shortened accordingly and a late ventricular pacing pulse that occurs when the long AV interval times-out without a sensed R-wave has a higher risk of creating a retrograde P-wave which could initiate a pacemaker mediated tachycardia (PMT). Thus, PVARP should be extended with a prolonged AV-hysteresis.

Hence, the need remains to more aggressively and effectively promote intrinsic conduction without the disadvantages of limiting the maximum tracking rate, not maintaining ventricular pacing support or creating longer periods of hemodynamic compromise. The present invention addresses these and other issues.

SUMMARY

What is described is an implantable cardiac stimulation device comprising a pulse generator that provides pacing pulses on demand to a heart chamber upon time-out of a delay interval and a timer that times the delay interval. The device further comprises an intrinsic conduction control circuit that extends the delay interval from a base delay interval to an extended delay interval and that maintains the extended delay interval as long as the pulse generator is inhibited for at least one cardiac cycle out of a given plural number of cardiac cycles.

The device may further comprise an R wave detector that inhibits the pulse generator upon detecting an R wave prior to time-out of a delay interval. The intrinsic conduction control circuit extends the delay interval from the base delay interval to the extended delay interval upon inhibition of the pulse generator.

The device may further comprise an interval timer that, upon timer expiration, times the period between return of the delay interval from the extended delay interval to the base delay interval and a next scheduled delay interval extension. The intrinsic conduction control circuit may extend the delay interval from the base delay interval to the extended delay interval upon inhibition of the pulse generator prior to time-out of the interval timer.

The extended delay interval may be one of a first extended delay interval and a second extended delay interval. The second extended delay interval is longer in duration than the first extended delay interval.

The intrinsic conduction control circuit may extend the delay interval from the first extended delay interval to the second extended delay interval upon the pulse generator being inhibited a consecutive predetermined number of cardiac cycles while the intrinsic conduction control circuit is extending the delay interval to the first extended delay interval. The intrinsic conduction control circuit may further extend the delay interval from the first extended delay interval to the second extended delay interval after the pulse generator is first inhibited for at least one cardiac cycle within a preselected number of cardiac cycles with the delay interval being the first extended delay interval. The intrinsic conduction control circuit may return the delay interval from the second extended delay interval to the first extended delay interval responsive to a predetermined event. The predetermined event may be the R wave detector detecting an R wave between the first and second extended delay intervals during a first number of cardiac cycles out of a last second number of cardiac cycles.

The invention further provides an implantable cardiac stimulation device comprising a pulse generator that provides pacing pulses on demand to a heart chamber upon time-out of a delay interval and a timer that times the delay. The device further comprises an intrinsic conduction control circuit that extends the delay interval from a base delay interval to a first extended delay interval and from the first extended delay interval to a second extended delay interval.

The intrinsic conduction control circuit maintains an extended delay interval as long as the pulse generator is inhibited for at least one cardiac cycle out of a given plural number of cardiac cycles.

The invention still further provides an implantable cardiac stimulation device comprising a pulse generator that provides pacing pulses on demand to a heart chamber upon time-out of a delay interval and a timer that times the delay interval. The device further comprises an interval extension timer that times an interval between delay interval extensions, and an intrinsic conduction control circuit that extends the delay interval from a base delay interval to an extended delay interval upon the first occurrence of one of time-out of the interval extension timer and pacing inhibition of the pulse generator.

The invention still further provides a method of pacing a heart comprising timing delay intervals, sensing R waves of the heart, and apply pacing pulses to the heart on demand in the absence of sensing an R wave before time-out of a corresponding delay interval. The method further comprises extending the delay interval from a base delay interval to an extended delay interval, and maintaining the extended delay interval as long as a pacing pulse is inhibited for at least one cardiac cycle out of a given plural number of cardiac cycles.

The invention further provides a method of pacing a heart comprising timing delay intervals, sensing R waves of the heart, apply pacing pulses to the heart on demand in the absence of sensing an R wave before time-out of a corresponding delay interval, and extending the delay interval from a base delay interval to a first extended delay interval and from the first extended delay interval to a second extended delay interval.

The invention further provides a method of pacing a heart comprising timing delay intervals, sensing R waves of the heart, and applying pacing pulses to the heart on demand in the absence of sensing an R wave before time-out of a corresponding delay interval. The method further comprises timing time periods between delay interval extensions, and extending the delay interval from a base delay interval to an extended delay interval upon the first occurrence of one of completion of timing of a time period between delay interval extensions and sensing an R wave before time-out of a corresponding delay interval.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
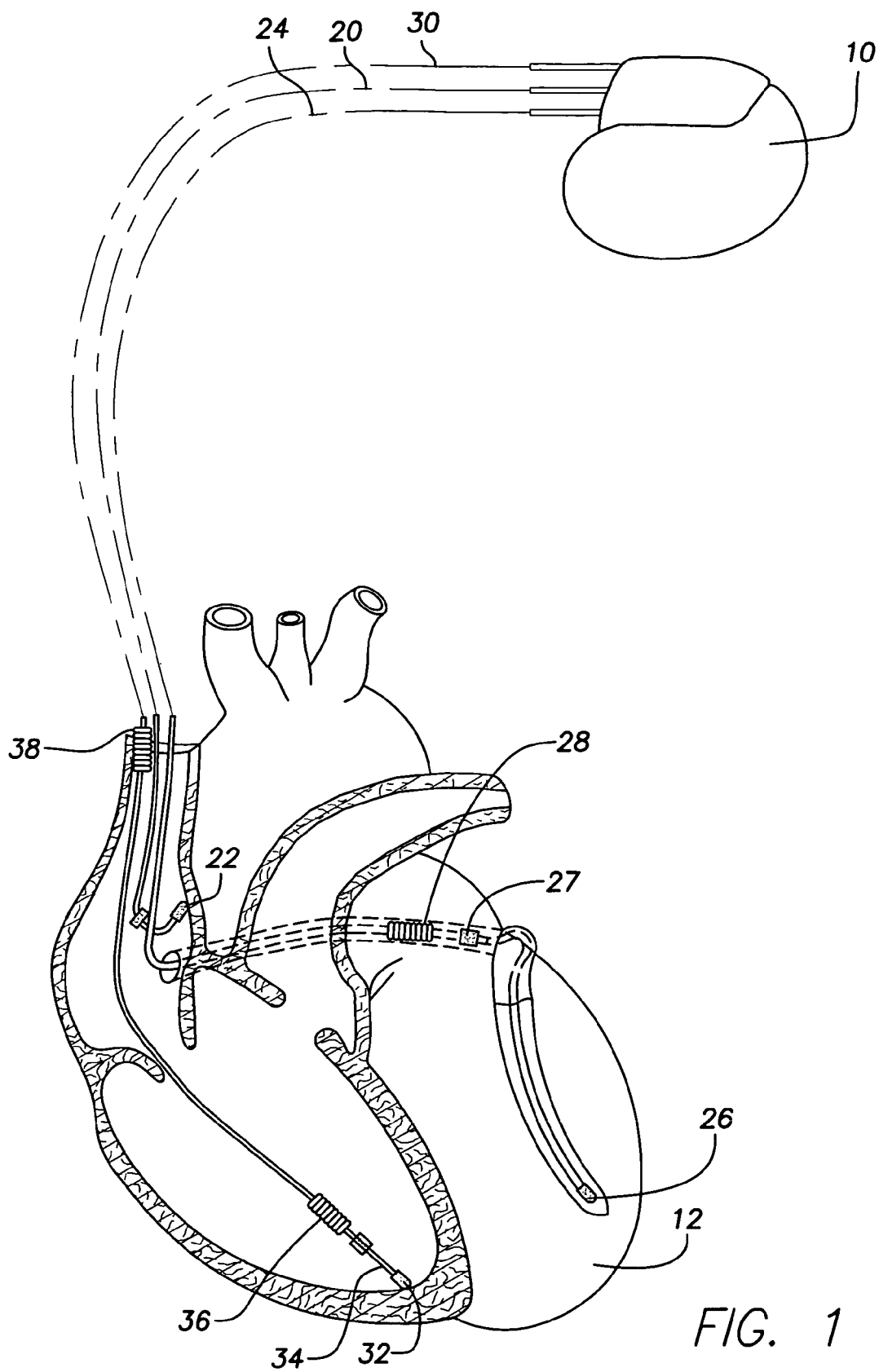
FIG. 1 is a simplified diagram illustrating an implantable stimulation device according to an embodiment of the present invention in electrical communication with a patient's heart.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
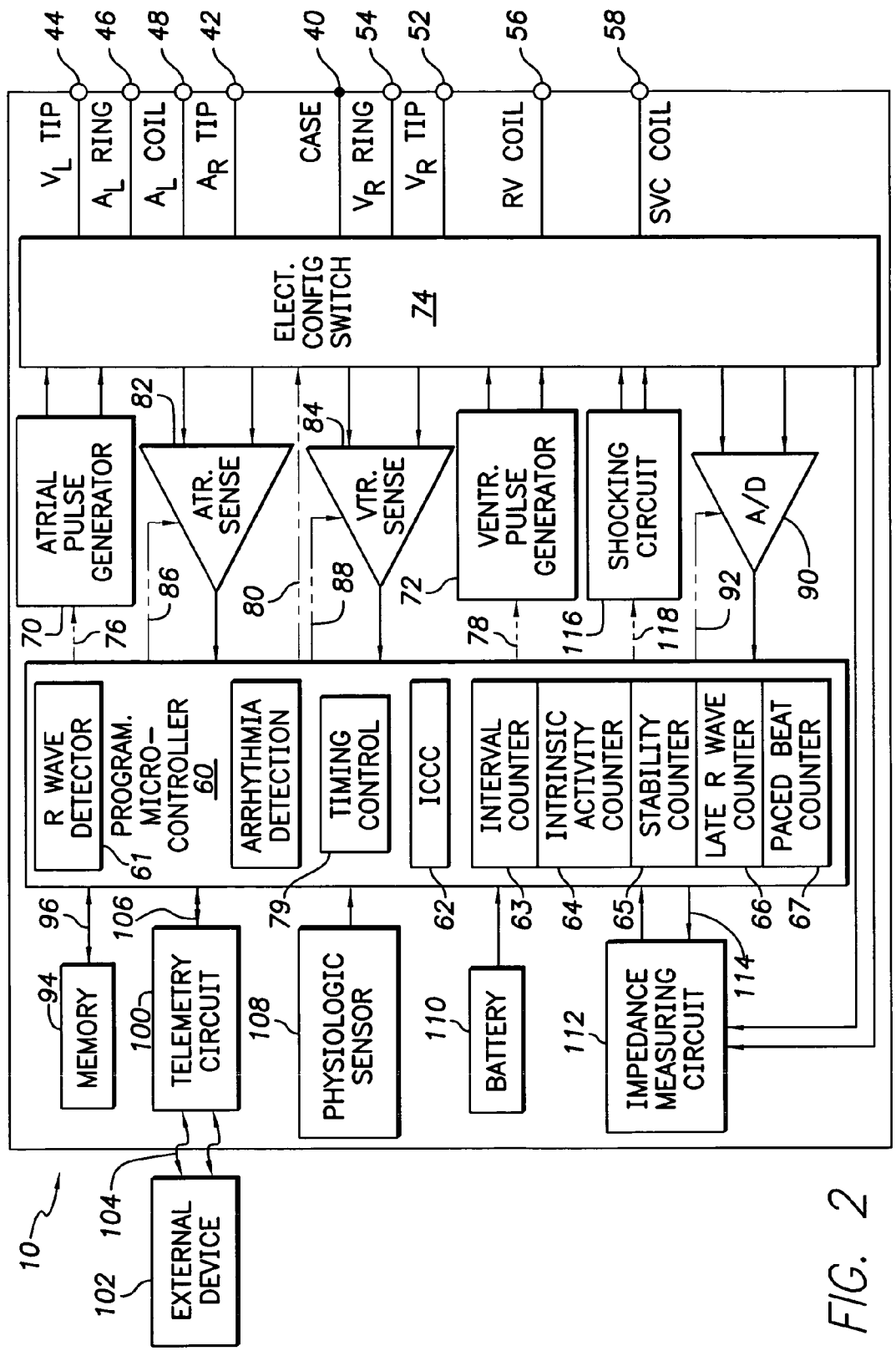
FIG. 2 is a functional block diagram of the implantable stimulation device of FIG. 1.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 may employ lithium/silver vanadium oxide batteries. A device which is a pacemaker only may have lithium iodine batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

With continued reference to FIG. 2, the device 10 further includes an R wave detector 61. The R wave detector 61 detects R waves of the heart and is primarily employed for supporting ventricular pacing on demand. More specifically, when an intrinsic atrial event (P wave) or an atrial pacing pulse (A wave) occurs, the timing control 79 commences to time an AV delay interval. If the timing control 79 completes the timing of an AV delay interval before an R wave is detected, a ventricular pulse generator 72 is called upon to issue a ventricular pacing pulse. However, if an R wave is detected before the timing control 79 completes the timing of the AV delay interval, the ventricular pacing pulse which would otherwise have been provided at the end of the AV delay interval is inhibited. Hereinafter, the term "paced beat" is meant to refer to a cardiac cycle in which a ventricular pacing pulse is provided and the term "intrinsic beat" is meant to refer to a cardiac cycle in which an R wave is detected before time-out of the AV delay interval and the scheduled delivery of a ventricular pacing pulse is inhibited.

To encourage and promote intrinsic activity of the heart, and according to this embodiment, the device 10 further includes an intrinsic conduction control circuit (ICCC) 62. The ICCC 62 promotes intrinsic ventricular activity of the heart by extending the AV delay interval to encourage intrinsic conduction. Such encouragement of intrinsic conduction is aggressively encouraged according to the present invention and as exhibited by first and second embodiments of the present invention.

In accordance with the first embodiment, the time in which the AV delay is extended is increased. Also, the probability of the appropriate condition for the AV delay interval extension is also increased. More specifically, instead of waiting for a search interval to complete before the AV delay interval is extended on schedule, if one or more intrinsic R waves occur, then ICCC 62 will immediately initiate an extension of an AV delay interval from a base AV delay interval to an extended AV delay interval. In addition, in the absence of an intrinsic beat before time-out of the search interval counter, upon time-out of the search interval counter, the ICCC 62 will extend the AV delay interval according to schedule.

In addition, according to the first embodiment, once the AV delay interval is extended, the interval extension is maintained as long as intrinsic activity is discerned. Such intrinsic activity discernment may be determined by the satisfaction of a condition calling for at least one intrinsic beat to occur out of a most recent given plural number of cardiac cycles. If this condition is satisfied, the AV delay interval extension will be maintained so long as the same or similar condition is satisfied. After the initial intrinsic activity is discerned, the required number of cardiac cycles in which one or more intrinsic beats must occur to maintain the AV delay interval extension may be increased or decreased.

The search intervals (the time between scheduled AV delay interval extensions) are timed by an interval counter 63. According to this embodiment, if one or more R waves occur before time-out of a search interval, the ICCC 62 immediately initiates an extension of the AV delay interval and the interval counter 63 is reset.

To count the intrinsic beats with the AV delay interval extension first in place, the device 10 includes an intrinsic activity counter 64. The condition for initial maintenance of the AV delay interval extension is the occurrence of the first one or more intrinsic beat(s) out of a most recent given plural number of beats. As soon as a required one or plural number of intrinsic beats occurs out of a given number of cardiac cycles, the AV delay interval extension is first maintained. Otherwise, the AV delay interval returns to the base AV delay interval.

Once the AV interval extension is first maintained, continued maintenance of the extended AV delay interval will be kept so long as at least one intrinsic beat is detected for every given plural number of beats. To detect the absence of such a condition being met, the device 10 includes a paced beat counter 67. If the paced beat counter counts the plural number of consecutive paced beats, the extended AV delay interval will be cancelled and the AV delay will be returned to the base AV delay.

Figure 3:
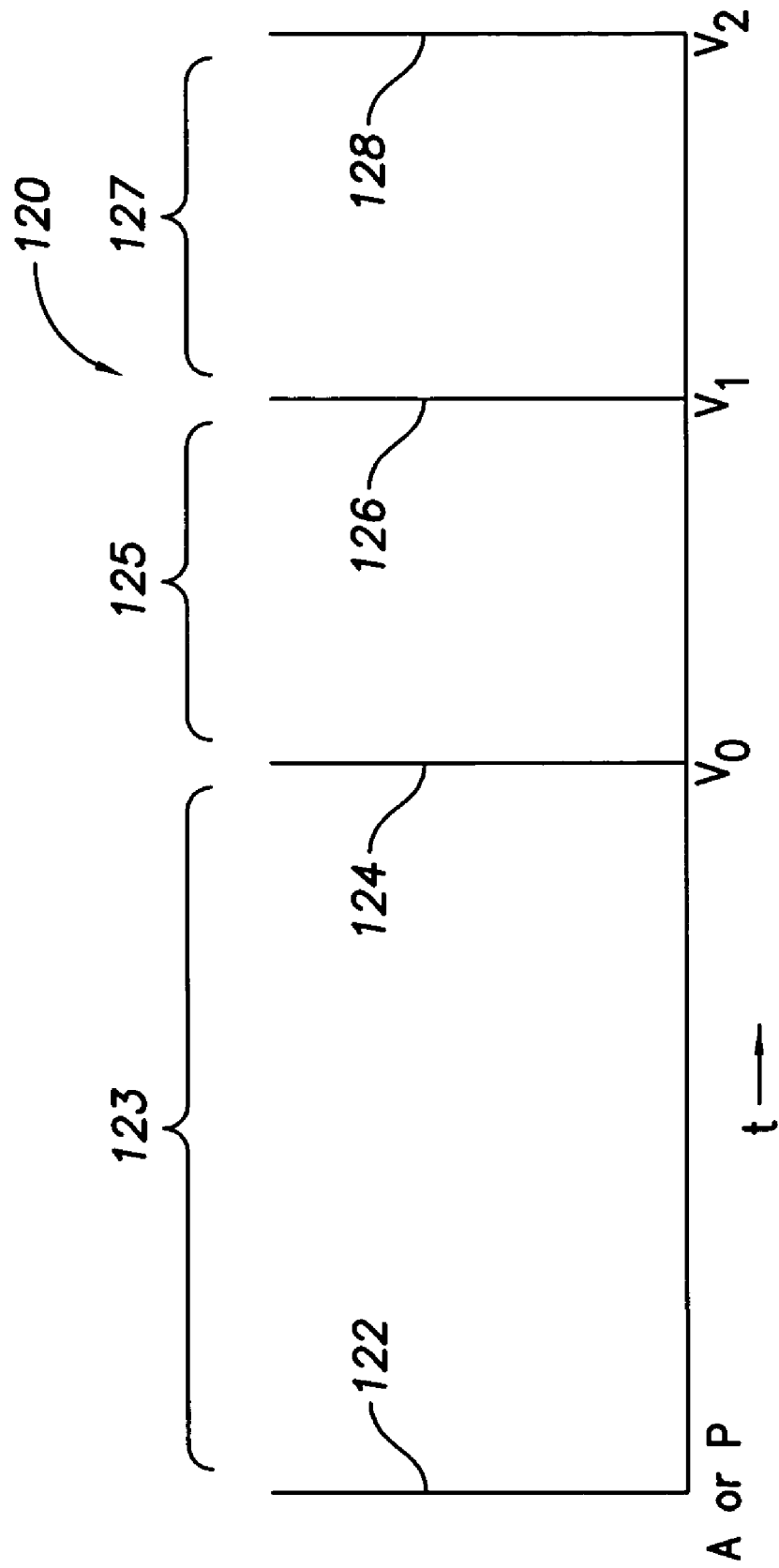
FIG. 3 is a time line illustrating a base AV delay interval, a first AV delay interval extension, and a second AV delay interval extension according to one embodiment of the present invention.

According to the second embodiment of the present invention, reference may be made to FIG. 3. FIG. 3 illustrates a timeline 120 illustrating the time 122 in which an atrial intrinsic event or an atrial paced event occurs, a base AV delay interval 123 which ends at a time 124 ($V_0$), a first AV delay extension 125 which ends at a time 126 ($V_1$), and a second AV delay interval extension 127 which ends at a time 128 ($V_2$). According to this embodiment, the AV delay interval may be initially extended from $V_0$ to $V_2$ or first extended from $V_0$ to $V_1$ and then, upon the satisfaction of a predetermined event, extended from $V_1$ to $V_2$.

In selecting the durations of the resulting AV delay intervals, the base AV delay interval $V_o$ is preferably selected to represent the hemodynamically optimal value for ventricular stimulation. The first extended AV delay interval $V_1$ is preferably selected to represent the maximum duration for intrinsic conduction that is acceptable for an individual patient for an unlimited period of time. Lastly, the second extended AV delay interval V2 is preferably selected to represent the maximum duration for intrinsic conduction that is acceptable for an individual patient for a limited period of time.

Since the second extended AV delay interval is preferably chosen to represent the maximum duration for intrinsic conduction that is acceptable for an individual patient for a limited period of time, the ICCC 62 will return the AV delay interval from the second extended AV delay interval to the first extended AV delay interval upon occurrence of a predetermined event or when a time limit is reached. According to this embodiment, the predetermined event or time limit may be the occurrence of a first number of R waves occurring between times $V_1$ and $V_2$ out of a last second number of cardiac cycles. When this occurs, the AV delay interval is returned to the first extended AV delay interval.

According to the embodiments herein, whenever an extended AV delay interval is in place and a preselected number of consecutive paced beats occur, the ICCC 62 returns the AV delay interval to the base AV delay interval $V_0$ whether the second extended AV delay interval $V_2$ or the first extended AV delay interval $V_1$ has been employed. Once the AV delay interval is returned to the base AV delay interval, the next AV delay interval extension will occur as described above.

In view of the foregoing, it may be noted in FIG. 2 that the device 10 further includes a stability counter 65, a late R wave counter 66, and a paced beat counter 67. The stability counter 65 counts consecutive intrinsic beats. According to the second embodiment herein, a consecutive predetermined number of intrinsic beats must occur with the first extended AV delay interval $V_1$ in place before the ICCC 62 extends the AV delay interval from a first extended AV delay interval $V_1$ to the second extended AV delay interval $V_2$. Late R waves are R waves occurring between time 126 and time 128. The late R wave counter 66 will thus count the number of R waves occurring between time 126 and time 128. When a first number of such late R waves are counted out of a last second number of cardiac cycles, the ICCC 62 will return the AV delay interval from the second extended AV delay interval $V_2$ to the first extended AV delay interval $V_1$.

Lastly, the paced beat counter 67 counts consecutive paced beats. According to either embodiment herein, when a consecutive number of paced beats occur while an extended AV delay interval is in place, the AV delay interval is returned to the base AV interval $V_0$.

Figure 4:
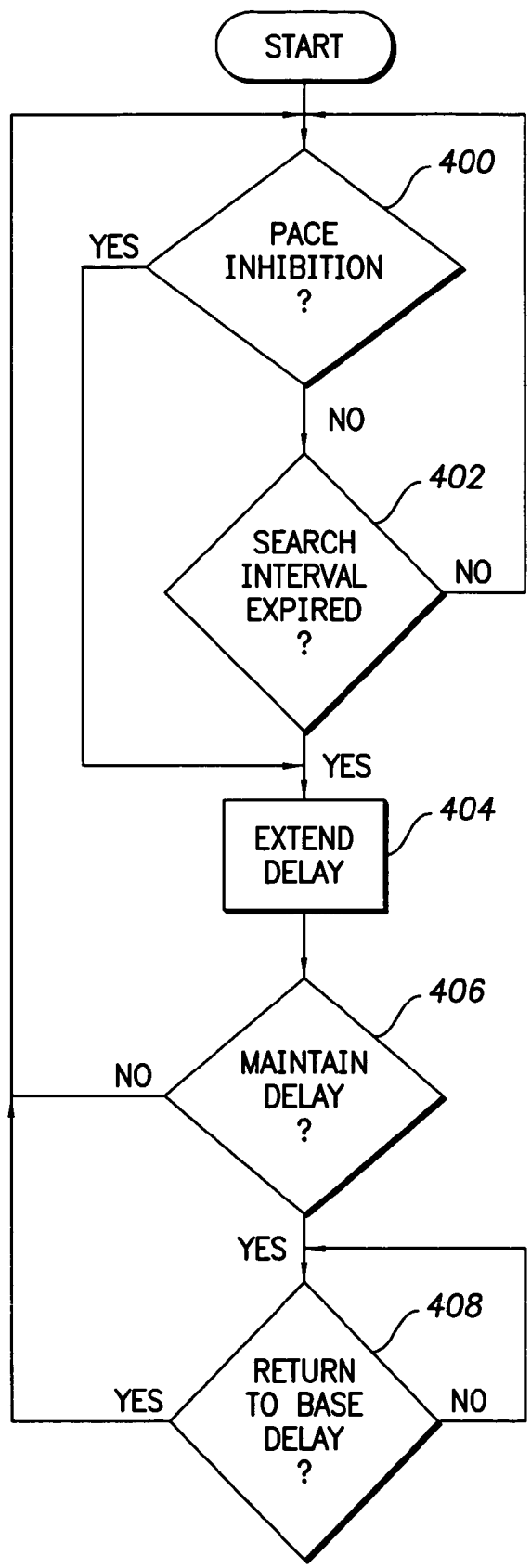
FIG. 4 is a flow chart describing an overview of the operation of one embodiment of the present invention.

Referring now to FIG. 4, FIG. 4 is a flowchart describing an overview of the operation and novel features implemented in one embodiment of the device 10. In this flowchart, and the flowchart of FIG. 5 described herein, the various algorithmic steps are summarized in individual "blocks". Such blocks describe specific actions or decisions that must be made or carried out as the algorithm proceeds. Where a microcontroller (or equivalent) is employed, the flowcharts presented herein provide the basis for a "control program" that may be used by such a microcontroller (or equivalent) to effectuate the desired control of the stimulation device. Those skilled in the art may readily write such a control program based on the flowcharts and other descriptions presented herein.

The process of FIG. 4 begins with a decision block 400 wherein it is determined if there has been a pacing pulse inhibition and thus an intrinsic beat. If there has not been an intrinsic beat, the process advances to decision block 402 to determine if the search interval has expired. As previously mentioned the search interval is timed by the interval counter 63 and is the time between the end of a last interval extension and a next scheduled interval extension. If the interval counter 63 has not timed out, the process returns to decision block 400. Upon the occurrence of an intrinsic beat or the time-out of the intrinsic counter 63, the process then advances to activity block 404 wherein the AV delay is extended. According to this embodiment, the AV delay may be extended from the base AV delay V0 to the first extended AV delay $V_1$. After the AV delay is extended, the process advances to decision block 406. In decision block 406 it is determined if the AV delay extension should be maintained. The maintenance of the extended AV delay may be conditioned upon the discernment of a certain level of intrinsic ventricular activity. For example, the AV delay extension may be maintained if a certain number of intrinsic beats, as for example one beat, occurs for a given plural number of cardiac cycles. If this condition is not satisfied, the process then returns to decision block 400. However, when one intrinsic beat occurs out of a given plural number of cardiac cycles, the extended AV delay interval is first maintained and the process then advances to decision block 408. Here, it is continuously determined if the AV delay extension should be further maintained or cancelled and returned to the base AV delay interval. The return of the AV delay interval to the base AV delay interval may be conditioned on a predetermined number of consecutive paced beats. Hence, counter 67 would be employed and when a predetermined number of consecutive paced beats occur, the AV delay interval will be returned to the base AV delay interval and, the process will return to decision block 400. As long as the predetermined number of consecutive paced beats does not occur, the extended AV delay interval will be maintained. The process will continue to monitor for such a condition.

Figure 5:
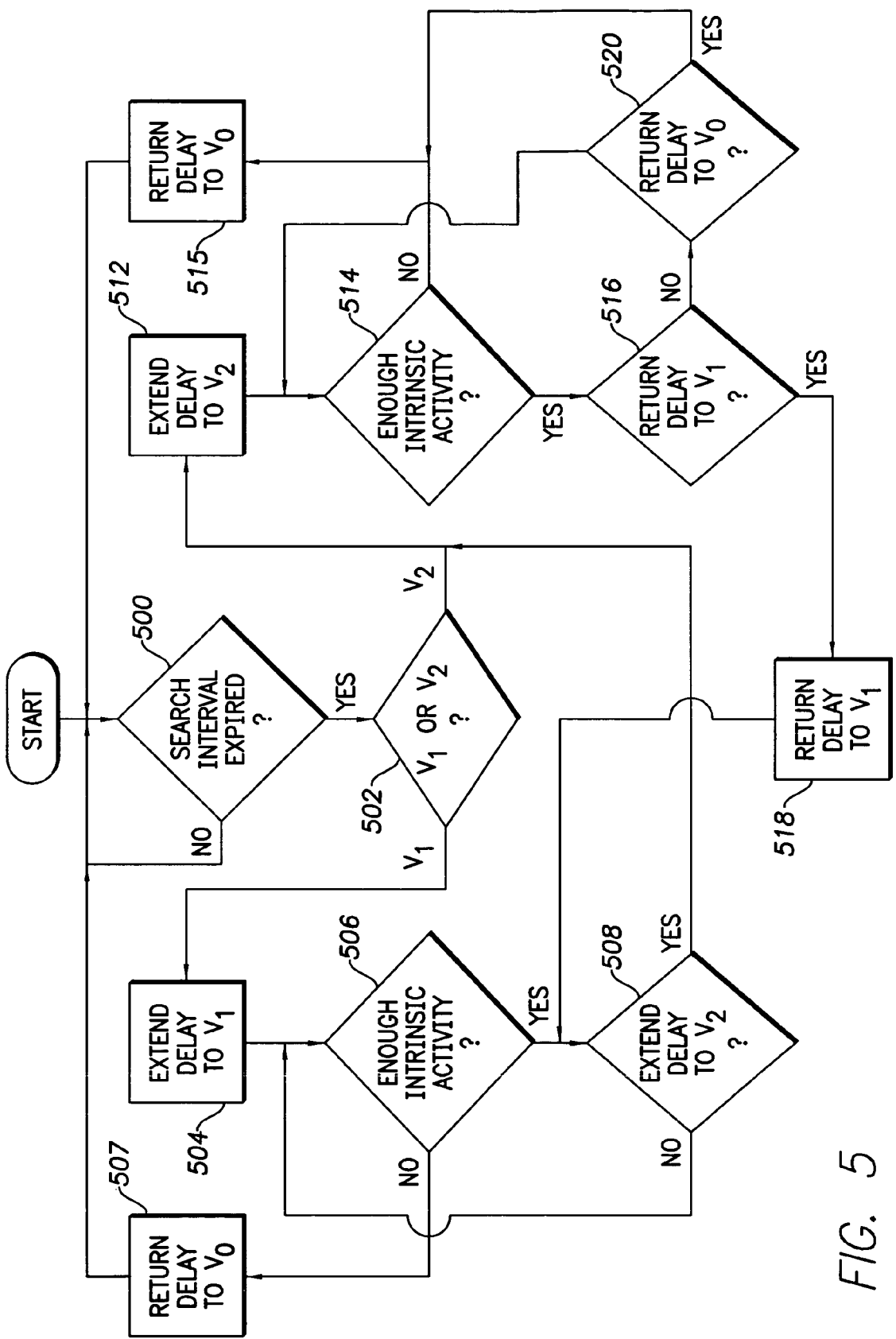
FIG. 5 is a flow chart describing an overview of the operation of another embodiment of the present invention.

Referring now to FIG. 5, it describes the overall operation of the second embodiment of the present invention disclosed herein. The process of FIG. 5 initiates with decision block 500 wherein it is determined if the search interval counter has timed out. If it hasn't, the process returns. If the search interval timer has timed out, indicating that a scheduled AV delay interval extension is to occur, the process advances to decision block 502. In decision block 502 it is determined if the device has been programmed to initially extend the AV delay interval to the first extended AV delay interval $V_1$ or initially extend the AV delay interval to the second extended AV delay interval $V_2$.

If the AV delay interval is to be initially extended to the first extended AV delay interval $V_1$, the process advances to activity block 504. In activity block 504, the AV delay interval is extended from the base AV delay interval to the first extended AV delay interval $V_1$. After the AV delay extension, the process advances to decision block 506. In decision block 506 it is determined if sufficient intrinsic activity exists at the first extended AV delay interval to first maintain the first extended AV interval or return the AV delay interval to the base AV delay interval $V_0$. In implementing decision block 506, the intrinsic activity counter 64 determines if at least one intrinsic beat has occurred out of a given plural number of cardiac cycles. If not, the process immediately advances to activity block 507 wherein the AV delay interval is returned from the first extended AV delay interval $V_1$ to the base AV delay interval $V_0$. The process then returns.

In further implementing decision block 506, as soon as the at least one intrinsic beat occurs within the given plural number of cardiac cycles, it is determined that sufficient intrinsic activity exists within the first AV delay interval extension $V_1$ to advance the process to decision block 508. Here it is determined if the AV delay should be extended to the second extended AV delay $V_2$.

In implementing decision block 508, the stability counter 65 counts intrinsic beats and looks for a consecutive predetermined number of intrinsic beats. If the predetermined number of consecutive intrinsic beats are found, the process then advances to activity block 512 wherein the AV delay interval is extended from the first extended AV delay interval $V_1$ to the second extended AV delay interval $V_2$. If the AV delay interval, as determined in decision block 508, is not to be extended to the second extended AV delay interval, the process advances back to decision block 506.

When the AV delay interval is extended to the second extended AV delay interval $V_2$, either from the base AV delay interval $V_0$ after implementation of decision block 502 or from the first extended AV delay interval $V_1$ after implementation of decision block 508, the process then advances to decision block 514. Here it is determined if there is sufficient intrinsic activity to maintain the second AV delay interval $V_2$. In implementing decision block 514, the intrinsic activity counter 64 may once again be employed for counting intrinsic beats. Again, it looks for the first one or more intrinsic beats within a predetermined number of cardiac cycles.

If insufficient intrinsic activity exists to initially maintain the second extended AV delay interval $V_2$, the process advances to activity block 515 wherein the AV delay interval is returned to the base AV delay interval $V_0$. However, if sufficient intrinsic activity does exists to initially maintain the second extended AV delay interval, the process advances to decision block 516.

In decision block 516 it is determined if the AV delay interval should be returned to the first extended AV delay interval $V_1$. Here, it is determined if the second extended AV delay interval has been maintained too long. More specifically, as previously described, the late R wave counter 66 is employed to count R waves falling between time 126, the end of the first extended AV delay interval $V_1$, and time 128, the end of the second extended AV delay interval $V_2$. If a first number of R waves fall between time 126 and time 128 out of a last second number of cardiac cycles, the process advances to activity block 518 wherein the AV delay is returned from the second extended AV delay $V_2$ to the first extended AV delay $V_1$. The process then returns to decision block 508.

If, however, the AV delay is not to be returned to the first extended AV delay $V_1$, the process then advances to decision block 520 wherein it is determined if the AV delay interval should be returned to the base AV delay interval $V_0$. Here, the paced beat counter 67 is once again employed to count paced beats. If a predetermined number of consecutive paced beats are counted, the process then advances to activity block 515 wherein the AV delay interval is returned to the base AV delay interval $V_0$. However, if the predetermined number of consecutive paced beats are not counted, the process then returns to decision block 514.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein. a1

What is claimed is:

1. An implantable cardiac stimulation device comprising:
 a pulse generator configured to provide pacing pulses on demand to a heart chamber upon time-out of a delay interval;
 a timer configured to time the delay interval;
 an intrinsic conduction control circuit configured to extend the delay interval from a base delay interval to an extended delay interval and that maintains the extended delay interval as long as the pulse generator is inhibited for at least one cardiac cycle out of a given plural number of cardiac cycles; and
 an interval timer that, upon time-out, is configured to time periods between return of the delay interval from the extended delay interval to the base delay interval and a next scheduled delay interval extension to the extended delay interval.

2. The device of claim 1 further comprising an R wave detector configured to inhibit the pulse generator upon detecting an R wave prior to time-out of a delay interval.

3. The device of claim 1 wherein the intrinsic conduction control circuit is configured to extend the delay interval from the base delay interval to the extended delay interval upon inhibition of the pulse generator.

4. The device of claim 1 wherein the intrinsic conduction control circuit is configured to extend the delay interval from the base delay interval to the extended delay interval upon inhibition of the pulse generator prior to time-out of the interval timer.

5. The device of claim 1 wherein the extended delay interval is one of a first extended delay interval and a second extended delay interval, wherein the second extended delay interval is longer in duration than the first extended delay interval.

6. An implantable cardiac stimulation device comprising:
a pulse generator configured to provide pacing pulses on demand to a heart chamber upon time-out of a delay interval;
a timer configured to time the delay interval;
an intrinsic conduction control circuit configured to extend the delay interval from a base delay interval to a first extended delay interval and from the first extended delay interval to a second extended delay interval; and
an interval timer that, upon time-out, is configured to time periods between return of the delay interval from the extended delay interval to the base delay interval and a next scheduled delay interval extension to an extended delay interval.

7. The device of claim 6, wherein the intrinsic conduction control circuit is configured to maintain an extended delay interval as long as the pulse generator is inhibited for at least one cardiac cycle out of a given plural number of cardiac cycles.

8. The device of claim 6 further comprising an R wave detector configured to inhibit the pulse generator upon detecting an R wave prior to time-out of a delay interval.

9. A method of pacing a heart comprising:
timing delay intervals;
sensing R waves of the heart;
apply pacing pulses to the heart on demand in the absence of sensing an R wave before time-out of a corresponding delay interval;
extending the delay interval from a base delay interval to an extended delay interval;
maintaining the extended delay interval as long as a pacing pulse is inhibited for at least one cardiac cycle out of a given plural number of cardiac cycles; and
timing time periods between return of the delay interval from the extended delay interval to the base delay interval and a next scheduled delay interval extension to the extended delay interval.

10. The method of claim 9 wherein the extending step includes extending the delay interval from the base delay interval to the extended delay interval upon inhibiting a pacing pulse.

11. The method of claim 9 wherein the step of extending the delay interval from the base delay interval to the extended delay interval is performed upon inhibition of the pulse generator prior to timing a next scheduled interval extension.

12. The method of claim 9 wherein the extended delay interval is one of a first extended delay interval and a second extended delay interval, wherein the second extended delay interval is longer in duration than the first extended delay interval.

* * * * *